Aug. 12, 1930. J. GLASS Re. 17,772

SUSPENDERS AND SPINAL SUPPORTER

Original Filed Jan. 7, 1925 3 Sheets-Sheet 1

Inventor

Jacob Glass,

By D. T. Wallace

Attorney

Aug. 12, 1930. J. GLASS Re. 17,772

SUSPENDERS AND SPINAL SUPPORTER

Original Filed Jan. 7, 1925 3 Sheets-Sheet 2

Inventor

Jacob Glass,

By D. P. Walker

Attorney

Aug. 12, 1930. J. GLASS Re. 17,772
SUSPENDERS AND SPINAL SUPPORTER
Original Filed Jan. 7, 1925 3 Sheets-Sheet 3
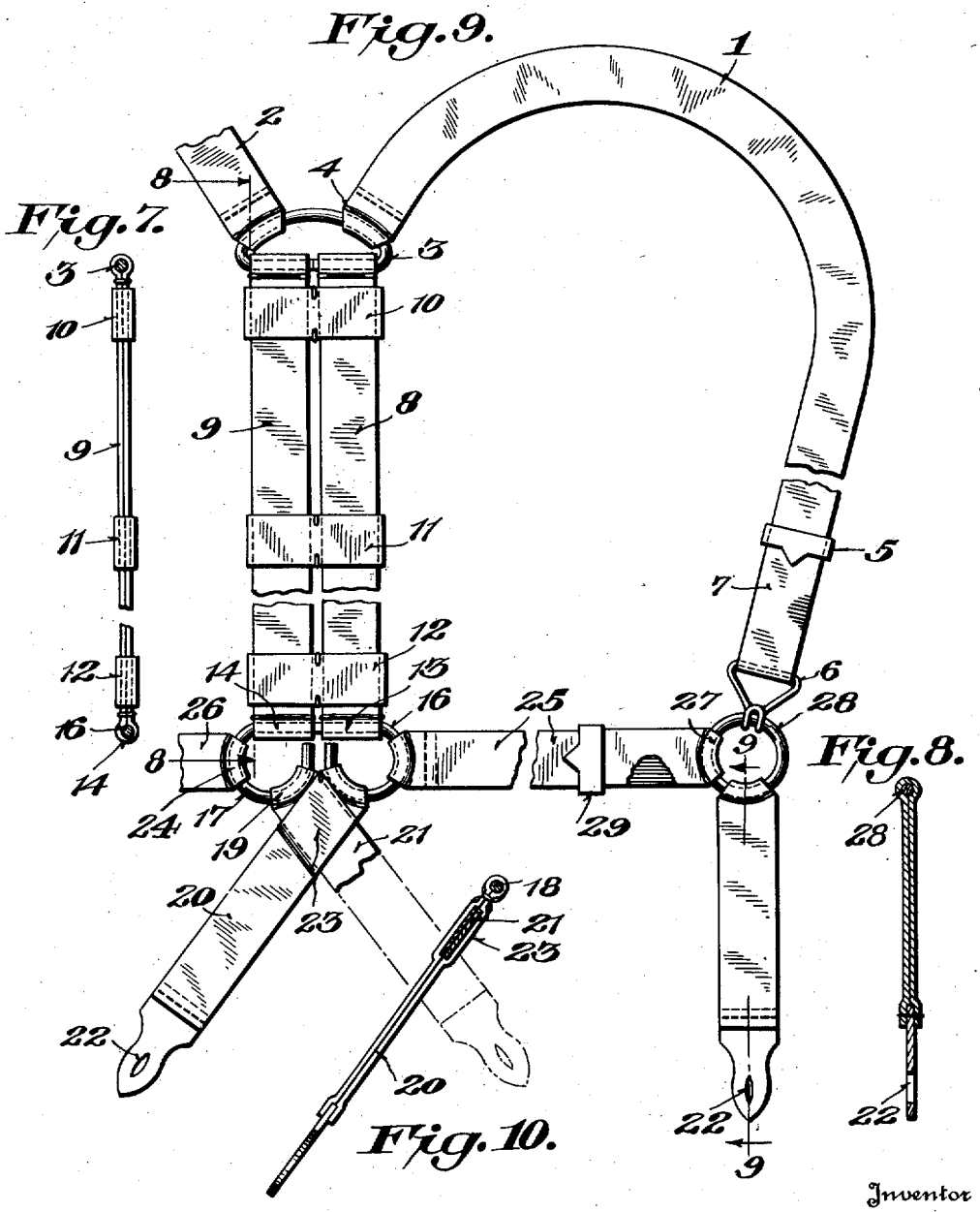
Inventor
Jacob Glass,
By D. P. Wolhaupter
Attorney Reissued Aug. 12, 1930 Re. 17,772

UNITED STATES PATENT OFFICE

JACOB GLASS, OF NEW YORK, N. Y.

SUSPENDERS AND SPINAL SUPPORTER

Original No. 1,715,196, dated May 28, 1929, Serial No. 974, filed January 7, 1925. Application for reissue filed July 24, 1929. Serial No. 380,739.

This invention relates to improvements in garment supporters, and one of the objects thereof is to provide a new and improved suspender and shoulder brace which is equally adapted to be worn by both sexes.

Another object of the invention is to provide a combined shoulder brace and suspender of the above character, such that the parts of the device located on the front part of the body are concealed, whereby they may be worn by both sexes without presenting an unsightly appearance upon the front portion of the body.

Other objects and aims of the invention, more or less specific than those referred to above, will be in part obvious and in part pointed out in the course of the following description of the elements, combinations, arrangements of parts and applications of principles, constituting the invention, and the scope of protection contemplated will be indicated in the appended claims.

In the accompanying drawings, wherein I have illustrated a preferred form of embodiment of my invention:

Figure 7 is a vertical sectional view taken on the line 8—8 of Figure 9.

Figure 8 is a view taken on the line 9—9 of Figure 9, looking in the direction of the arrows.

Figure 9 is a fragmentary elevation of the device as disclosed in Figure 2.

Figure 10 is a longitudinal sectional view taken through one of the tabs.

Figure 1:
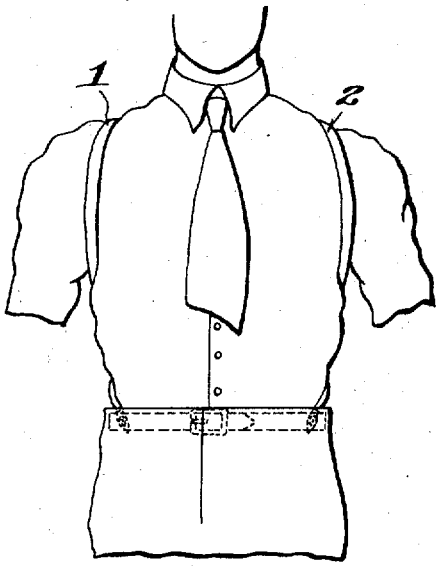
Figure 1 is a front elevational view of a male figure, showing my improved device mounted thereon.
Figure 2:
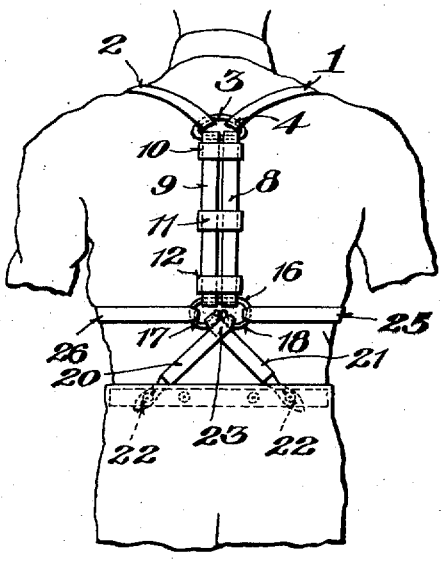
Figure 2 is a rear view of the same figure, showing the back of the device.
Figure 3:
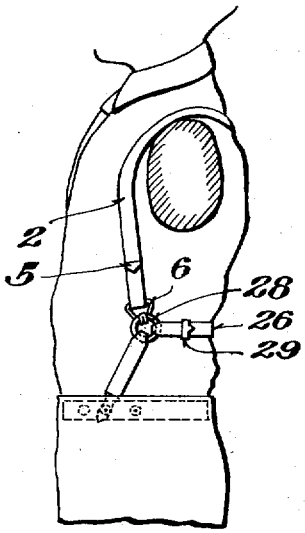
Figure 3 is a side elevational view of the same figure.
Figure 4:
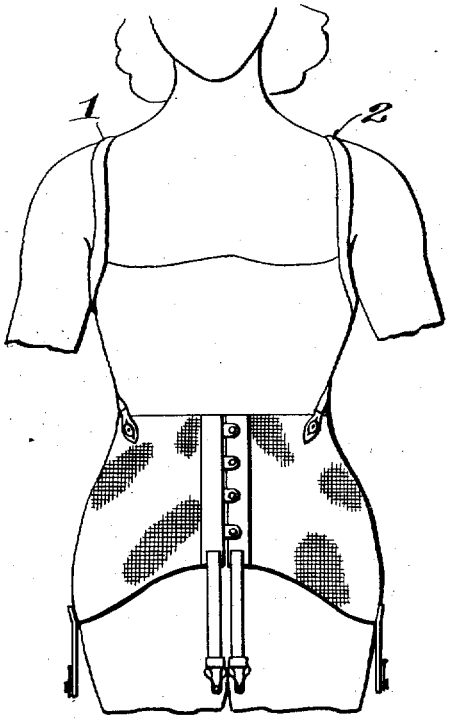
Figure 4 is a front elevational view of a female showing my device used in connection with a corset.
Figure 5:
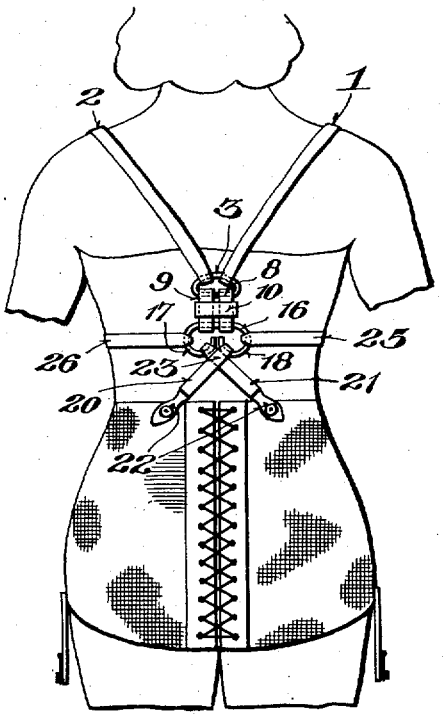
Figure 5 is a rear view of the same female figure.
Figure 6:
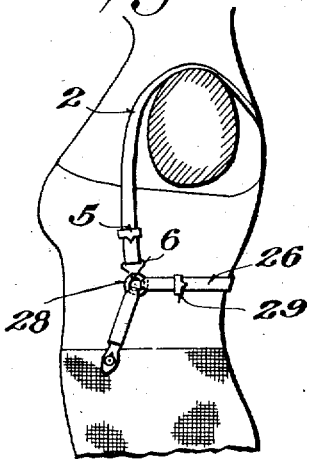
Figure 6 is a side elevational view of the same female figure.

Referring now to the drawings, wherein similar reference characters refer to similar parts throughout the several views thereof, the reference numeral 1 denotes one of the suspending straps, the same preferably comprising a band of webbing, which may be formed of elastic, if desired. The reference numeral 2 denotes a similar band. These bands, which are adapted to extend over the shoulders of the wearer in the usual manner of wearing suspenders, are connected at their rear ends at a point preferably slightly above the middle of the back of the wearer, with a ring 3, the connection being made as by means of the loops 4 sewed in the ends of the webbing, whereby said ends have a sliding connection with the ring 3. Each band preferably adjacent the front end thereof, is provided with an adjusting device 5, similar to that usually employed in suspenders.

The front end of each band is provided with a hook 6, which hook preferably extends through a loop 7, formed in the front end of the strips 1 and 2, which loops co-operate with the adjusting devices 5 to take up the material of the webbing, as when it is desired to adjust the device.

Extending downwardly and looped about the ring 3, are the strips of webbing 8 and 9, also formed of elastic material, said loops being preferably provided with the spacing members 10, 11 and 12. The lower ends of these strips 8 and 9 are provided with looped portions 13 and 14, which are doubled over the straight leg of a double ring 16, the ring portion thereof being indicated at 17 and 18. Slidably mounted upon the ring portions 17 and 18, as by means of loops 19 formed in the material, are straps 20 and 21, the lower ends of which in the present instance are provided with buttonholes 22, so that these straps may be attached to buttons or the like fastened upon the garment to be supported. These straps cross each other at the point 23.

Connected to each of the rings 17 and 18, as by means of loops 24, are the side straps 25 and 26, which straps extend laterally and forwardly, and are connected as by means of the adjustable loops 27, with the rings 28. Each of the straps 25 and 26 is provided with an adjusting device 29, by means of which the loops 27 may be lengthened or shortened.

In Figure 8 I have illustrated the form of tab or strap which is preferably employed in the front portion of the device. This strap or tab comprises the certain material looped around the ring 28, the legs of the loop extending downwardly and being stitched to the member provided with the buttonhole 22, which engages the garment.

While the manner of using my device will be clearly understood from the drawings, it will be observed that the device functions not only as a garment supporter, but also a shoulder brace, the side straps 25 and 26, which may also be made of elastic webbing, pull the front suspending parts of the device outwardly and rearwardly, so that no part thereof is exposed on the front portion of the body of the wearer. Thus the device can be worn by the male sex in summer, without a waistcoat, the suspending parts being practically invisible; and in winter with dress clothes. It may also be worn by women with evening clothes, inasmuch as the only parts of the device visible from the front are the parts extending over the shoulders. The side straps, in combination with the suspending parts of the device, act efficiently as a shoulder brace, holding the body straight and erect.

In this connection it is obvious that while the device is primarily intended as a garment supporter, it may be worn to advantage with any suitable waistband whether said band constitutes a portion of a garment, as herein illustrated, or whether same is constituted by an element such as a belt or the like entirely independent of a garment. In either instance, due to the straps 1 and 2 being connected at their front ends to front portions of the waistband, at their rear ends to rear portions of the waistband, and with one another by the straps 25, 26 which extend under the arms and across the back of the person wearing the device, the shoulders of the wearer are supported by the straps 1 and 2 against drooping forwardly and the body of the wearer is, as aforesaid, held erect.

As many changes could be made in this construction without departing from the scope of the following claims, it is intended that all matter contained in the above description or shown in the accompanying drawing shall be regarded as illustrative only and not in a limiting sense.

I claim:

1. In a garment supporter, a pair of strips of elastic webbing adapted to be passed about the shoulders of the wearer, a pair of downwardly extending straps to which the rear end of said strips have a common ring connection therewith, the front ends of each of said strips being provided with a hook member, a pair of rings, each of which is adapted to be engaged by one of said hook members, a strap connected with each of said rings, a double ring member to which each of said downwardly extending straps is connected, side straps connecting said double ring with each of said first named rings, and a plurality of garment engaging straps attached to said double ring.

2. A combination garment supporter and shoulder brace, comprising a pair of straps adapted to be passed over the shoulders of the wearer, the forward end of said straps being adjustable and having a hook portion, a ring for receiving each of said hooks, a garment supporting strap connected with each of said rings, the rear portion of each of said first named straps being provided with a ring portion, straps extending downwardly from said ring, a double ring to which each of said last named straps is connected, a plurality of garment supporting straps connected with said double ring, and laterally extending adjustable straps connecting said double ring and said first named rings.

3. A device of the character described comprising a pair of flexible elements adapted to extend, respectively, over the shoulders of the wearer of the device and to have their front ends connected with front portions of a garment, a strap adapted to lie against the back of the wearer of the device, a common ring connection between the rear ends of said shoulder elements and the upper end of said strap, a ring member at the lower end of said strap, straps connected at their upper ends with said ring member and adapted for connection at their lower ends with rear portions of the garment, and side straps connected at their rear ends with said ring member and at their forward ends with front portions of said shoulder straps.

In testimony whereof I hereunto affix my signature.

JACOB GLASS, M. D.